United States Patent [19]

Quirk et al.

[11] Patent Number: 4,978,793

[45] Date of Patent: Dec. 18, 1990

[54] NOVEL PROCESS FOR THE PREPARATION OF SERINOL

[75] Inventors: Jennifer M. Quirk, Highland; Stephen G. Harsy, Mt. Airy, both of Md.; Christer L. Hakansson, Helsingborg, Sweden

[73] Assignee: W. R. Grace & Co.-Conn., New York, N.Y.

[21] Appl. No.: 210,945

[22] Filed: Jun. 23, 1988

[51] Int. Cl.$^5$ ............................................ C07C 209/00
[52] U.S. Cl. .................................. 564/487; 549/371; 568/712
[58] Field of Search .................. 549/371; 564/487; 568/712

[56] References Cited

U.S. PATENT DOCUMENTS

| | | | |
|---|---|---|---|
| 2,383,622 | 8/1945 | Senkus | 260/338 |
| 2,415,021 | 1/1947 | Morey | 260/338 |
| 2,485,987 | 10/1949 | Senkus | 167/33 |
| 2,500,155 | 10/1948 | Croxall et al. | 260/338 |
| 3,020,319 | 2/1962 | Klager | 260/635 |
| 3,459,771 | 8/1969 | Nikles et al. | 260/340.7 |
| 3,560,575 | 2/1971 | Tindall | 260/635 |
| 3,845,130 | 10/1974 | Suggitt | 260/583 M |
| 4,221,740 | 9/1980 | Pfeiffer | 260/584 R |
| 4,233,245 | 11/1980 | Bourguignon et al. | 564/506 |
| 4,448,999 | 5/1984 | Thewalt et al. | 564/495 |
| 4,613,606 | 9/1986 | Clark et al. | 514/307 |

FOREIGN PATENT DOCUMENTS 2829916 7/1978 Fed. Rep. of Germany.

OTHER PUBLICATIONS

Roczniki Chemmii. Ann. Soc. Chim. Polonorum 47 409 (1973).

Preparation of 2-and 5-Substituted-1,3-Dioxanes by G. B. Linden et al. J. Org. Chem. 21 1175 (1956).

Linden et al. "Preparation of 2-and 5-Substituted-1,3--Dionxanes" *J. Org. Chem.* 21 1175-6 (1956).

Piotrowska et al. "Michael Addition of a 5-Nitro-1,-3-Dioxane Roczniki Chemmii." Ann. Soc. Chim. Polonorum 47 409 (1973).

*Primary Examiner*—Glennon H. Hollrah
*Assistant Examiner*—Peter G. O'Sullivan
*Attorney, Agent, or Firm*—Howard J. Troffkin

[57] ABSTRACT

A process of forming 2-amino-1,3-propanediol by reducing the compound, 5-nitro-1,3-dioxane and subsequently hydrolyzing the reduced compound.

10 Claims, No Drawings

NOVEL PROCESS FOR THE PREPARATION OF SERINOL

BACKGROUND OF THE INVENTION

The present invention relates to a novel process to form 2-amino-1,3-propanediol (commonly known as "serinol"). The present process provides a means of forming serinol using readily formed materials under mild and easily handled conditions suitable for industrial application.

Serinol is a highly desired material required for the preparation of nonionic x-ray contrast media, such as iopanediol (N,N'-bis[2-hydroxy-1-(hydroxymethyl)ethyl]-2,4,6-triiodo-5-lactamidisophthalamide).

Serinol has been previously prepared from 2-oximino-1,3-propanediol, 2-nitro-1,3-propanediol, serine, serine methyl ester, or oximinomalonic acid diethyl ester. In most cases the required processes provided low yields and, in certain instances, utilizes poorly accessible starting materials. In addition, the processes normally entail the generation of decomposable and dangerous intermediates which require special equipment and handling practices. The expense of the reactants and equipment required, as well as the special handling needed leads to unsatisfactory processes for industrial application.

The major commercial method of producing serinol is disclosed in U.S. Pat. No. 4,448,999 and involves an improvement of a process disclosed in DE No. 2,742,981. The process requires the initial formation of a solid product, sodium nitro-1,3-propanediol. The diol must be removed from the reaction zone in order to minimize unwanted further reaction to the triol. The diol is then subjected to hydrogenation at elevated pressures of 50 bars or greater in the presence of palladium on carbon as the hydrogenation catalyst. U.S. Pat. No. '999 discloses that the hydrogenation process should be carried out under stringent temperature conditions to achieve consistently good yields. The difficulty with this method is the need for isolating and utilizing sodium nitro-1,3-propanediol which is known to be an unstable material which decomposes with catastrophic results.

An alternate method for producing serinol is disclosed in DE No. 2,829,916. This process involves the reductive amination of 1,3-dihydroxyacetone. Due to the difficulty in synthesizing the required starting ketone, this process is not economically competitive and is not widely used on an industrial scale.

It is highly desired to have a process capable of forming serinol which utilizes readily available and easily handled materials.

SUMMARY OF THE INVENTION

The present invention is directed to a process which is readily adaptable to industrial application and utilizes reactants and conditions which do not present a handling problem.

The instant process comprises hydrogenation of certain 5-nitro-1,3-dioxanes under mild conditions to form the corresponding amino derivatives and hydrolyzing the amino derivatives to give the desired serinol.

DETAILED DESCRIPTION OF THE INVENTION

The present process provides the desired serinol using readily available reactants under conditions easily adaptable for industrial application.

The total synthesis can be accomplished by the following reactions:

1. Nitromethane is reacted with three moles of formaldehyde to form tris(hydroxymethyl)nitromethane (I).

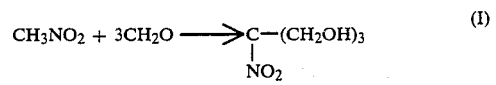

This Henry Reaction is carried out by contacting the nitromethane and formaldehyde in a solvent normally selected from a lower alkyl alcohol or water (preferably methanol) in the presence of a catalytic amount of base such as sodium or potassium hydroxide. The formaldehyde should be present in at least stoichiometric amounts based on nitromethane (i.e. 3 moles of formaldehyde per mole of nitromethane). This reaction is known and the product can be commercially obtained. This product, unlike the dihydroxymethyl nitromethane sodium salt used in U.S. Pat. No. '999, is a stable product which is readily obtained in very high (90%) yields because the substitution is allowed to go to completion.

The formaldehyde and nitromethane can be contacted in less than a 3:1 molar ratio provided the reaction product is not isolated but, instead, the product solution is used directly in step two described below and, in turn, the product solution of step 2 is used in step three, as also described below. The formaldehyde and nitromethane can be used in molar ratios of about 2.25 or greater. When used in molar ratios of less than 3, the resultant solution will contain a mixture of di and trihydroxymethyl nitromethane. The product should not be isolated but, instead, the solution should be directly treated with a ketone or an ether as described below in the presence of an acid (sufficient to neutralize the small amount of base present and to make the solution acidic). The solution containing the products of this procedure should be directly used in the procedure of step three to provide product III.

When the molar ratio is greater than 3, the products of steps 1 and 2 may be isolated or the solution may be directly used in the subsequent step.

2. The formed tris(hydroxymethyl)nitromethane (I) is then reacted with a ketone in the presence of a catalytic amount of a strong acid to form the corresponding acetal, the 5-hydroxymethyl-5-nitro-1,3-dioxane which has substitution in the 2 position (II), in good yields.

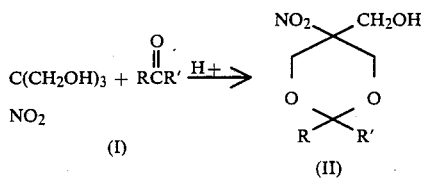

Each R and R' can independently be selected from an alkyl, cycloalkyl or aryl group or R and R' can together form an alkylene group, and preferably a $C_4$-$C_6$ alkylene group The particular identity of R and R' is not critical to this reaction nor to the overall synthesis. Examples of suitable ketones include acetone, methyl ethyl ketone, diethyl ketone, cyclohexanone and the like. The reaction can be run neat using excess ketone as the reaction medium (preferred) or by using an inert solvent in which both compound I and the ketone are soluble. The reaction is catalyzed by the presence of catalytic amounts (normally from about 0.001 to 1 weight percent based on the weight of ketone) of a strong acid, such as a mineral acid (HCl, $H_2SO_4$ and the like) or a strong organic acid such as glacial acetic acid, toluene sulfonic acid and the like.

The above reaction (2) produces water as a by-product. The water must be removed in order to prevent reversion of the formed acetal back to the ketone and alcohol. When the reaction utilizes a high boiling ketone (having a B.P. higher than water and suitable for separating the water from ketone by distillation), such as cyclohexanone, the water by-product can be removed by azeotropic distillation during the progress of the reaction. When a low boiling ketone, having a boiling point lower than water, such as acetone, is used the procedure requires the presence of a dessicant, such as boron triflouride etherate or a molecular sieve which collects water to remove the water as it forms.

Although the above reaction utilizes readily attainable and inexpensive reactants, the need to remove the water by-product as it forms may add to the cost of the reaction and the overall synthesis. If such economics presents a factor, the formation of an acetal can be accomplished without the production of water by alternate reactions, as described hereinbelow.

2(A). The tris(hydroxymethyl)nitromethane (I) can be converted to an acetal by reacting it with a vinyl ether in the presence of a catalytic amount of a strong acid (such as mineral acids, glacial acetic acid and the like) by the following reaction:

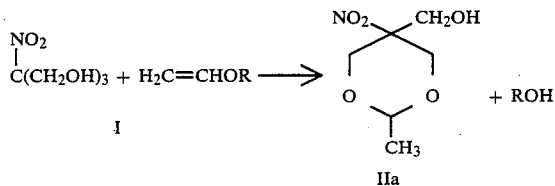

R can represent any alkyl, cycloalkyl or aryl group and is preferably a lower alkyl. Examples of suitable vinyl ethers include ethyl vinylether, methyl vinylether and the like. The resultant by-product alcohol does not interfere with the reaction.

2(B). Again, as an alternate means, the desired acetal compound can be provided by reacting the tris(hydroxymethyl)nitromethana (I) with certain gem diethers in the presence of a catalytic amount of a strong acid (such as mineral acid, glacial acetic acid and the like) by the following reaction:

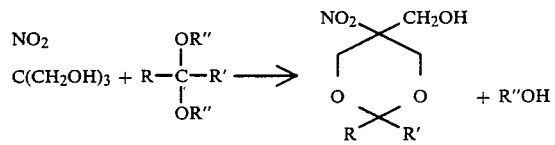

The symbols, R and R' are the same as described above with respect to reaction 2 and R'' can be any alkyl, preferably a lower alkyl such as methyl, ethyl, propyl and the like. Examples of such gem ethers include 2,2-dimethoxypropane 2,2-diethoxypropane, 3,3-dimethoxypentane, 3,3-diethoxy pentane and the like.

The reaction 2A and 2B can be carried out by taking up compound I in excess of the ether and warming the system to a temperature of from about 20° C. to 80° C. with temperatures of from 20° C. to 50° C. being preferred.

The resultant acetals, (II), (IIa) and (IIb), are all readily formed in good yields which is normally greater than about 90 percent. The acetal can be separated from the reaction mixture by conventional means such as by distillation where the product is a liquid or by filtration where the product is a solid. The exact nature of the product depends on the identity of R and R'.

3. The 5-hydroxymethyl-5-nitro-1,3-dioxane derivatives (II), (IIa) or (IIb) are readily converted into the corresponding 5-nitro-1,3-dioxane compound by treating the derivative with alkali, such as an alkali (preferably) or alkaline earth metal hydroxide (MOH), and then acidification of the solution according to a procedure suggested in Roczniki Chemii Ann. Soc. Chim. Polonorum 47 409 (1973) as represented by the conversion of II as follows:

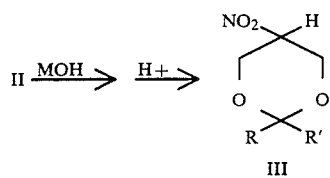

The reaction can be carried out by taking the acetal up in an aqueous solution of an alkali metal hydroxide such as sodium or potassium hydroxide. The hydroxide concentration may be from about 5 to 25 percent or greater with from 10 to 20% being preferred. The presence of excessive amounts of water (above that required to retain a solution) should be avoided. The solution should be agitated as by stirring for a period of time of from 10 minutes to 200 minutes, with from about 30 to 100 minutes normally being satisfactory, while maintaining an elevated temperature of from about 30° to 100° C. (40°-80° C. being preferred). The solution is then cooled to a reduced temperature to less than about 20° C. and preferably from about 0° C. to 20° C. prior to slow introduction of the acid. Although concentrated mineral acid can be used, it is preferred to use an organic acid such as acetic acid or the like, to minimize the water concentration and thereby enhance the precipitation of product III which can be readily separated by conventional means such as filtration. When IIa is used the resultant product will be the corresponding 2-methyl-5-nitro-1,3-dioxane (IIIa).

4. The 5-nitro-1,3-dioxane derivative III, whether formed by the above synthesis route or by other methods (such as one proposed by Linden et al., J. Org. Chem. 21 1175 (1956) by direct cyclization of 2-nitro-1,3-propanediol) has been found to be convertible into serinol. The process requires the hydrogenation of product III under specific conditions to form the corresponding 5-amino-1,3-dioxane derivative (IV) by the following reaction:

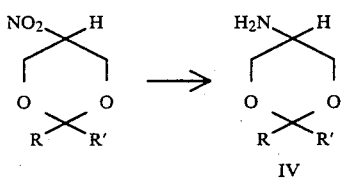

The hydrogenation must be conducted under mild conditions with controlled temperature and pressure conditions and in the presence of certain specific catalysts, as described below.

The hydrogenation can be conducted by taking up product III in an inert liquid capable of solvating product III. Such solvent can be readily determined with minimum conventional procedure for any particular product III and include water and lower alkyl alcohols as, for example, methanol, ethanol, propanol and the like; ethers such as diethyl ether, tetrahydrofuran and the like; aliphatic and aromatic hydrocarbon such as hexane, toluene, benzene and the like. The product III is dissolved in the solvent. The solvent/product III mixture is placed in a suitable reactor capable of withstanding the mild pressurized reaction conditions. Product III is hydrogenated with hydrogen gas at pressures of from about 15 psi to 2000 psi with from about 25 to 200 psi being found suitable in most instances. Greater pressure may be used but is unnecessary. The reaction mixture should be maintained at moderate temperatures of from about 30° C. and 100° C. with from 60° C. to 90° C. being preferred. The hydrogenation will proceed in the presence of a catalyst which can be selected from any conventional heterogeneous hydrogenation catalyst. The catalyst may be of the supported or unsupported type and formed from a Group VIII metal. The unsupported catalyst can be in the form of finely divided metal or metal oxide. The support catalyst are formed from a Group VIII metal on a conventional support, such as carbon, silica, clays, and the like. In addition, Raney nickel can be used as a catalyst in the present process. The preferred catalysts are selected from Raney nickel (a nickel-aluminum alloy which was prior subjected to caustic removal of aluminum from the surface) or supported catalysts of rhodium, platinum or palladium such as Rh/C, Pt/C, Pd/C and the like. The catalyst should be present with respect to product III in amounts of from 0.2 to 10 weight percent and preferably from 0.5 to 7 weight percent. The reaction can be run as a batch reaction in an closed reaction vessel capable of maintaining the above temperature and pressure conditions and with the catalyst being slurried in the liquid mixture. Alternately, the reaction can be carried out in a continuous manner by passing a solvent/product III liquid mixture through a tubular reactor which is packed with catalyst and equipped with needed regulator valves to maintain the desired pressure, in manners conventionally known.

The 5-amino-1,3-dioxane derivatives(IV) which result from the hydrogenation can be used in the solvent in the final step. The product IV solution can thus be filtered to remove any catalyst material and the resultant liquid carried forward. Alternately, product IV is recovered by filtering the reaction solution (where appropriate, as with the slurry method described above) to remove catalyst material. The solvent and product IV are then separated by removing the lower boiling solvent from the product solution under mild temperature (preferably less than 150° C.). This can be done by various conventional means, such as be evaporation or distillation under atmospheric or subatmospheric pressure conditions. The resultant product IV can be used in the final process step described below.

An alternate means of conducting the mild hydrogenation of product III is to take product III up in an inert solvent as discussed above and, with a supported catalyst of rhodium, platinum or palladium, as disclosed above (preferably Pd/C), to hydrogenate product III using ammonium formate as the hydrogenating agent. The ammonium formate should be introduced into the reaction liquid in about three or more moles (preferably three to five moles) per mole of product III. Product IV is formed in high yields using this mild hydrogenating agent. The product need not be separated from the solution before proceeding with the final reaction to form serinol or may be separated in the manner described above.

5. Serinol is recovered in good yields by contacting product IV with a strong acid.

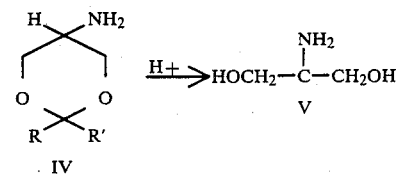

The formation of serinol from product IV proceeds readily by taking product IV up in water or a lower alkyl alcohol such as methanol (preferred), ethanol, propanol or the like to provide a solution and introducing a mineral acid such as hydrochloric, nitric, sulfuric acid into the solution. Although the exact mode of contacting the acid and product IV is not critical, it is preferred that the acid be introduced slowly and the solution be maintained at moderate temperatures such as ambient to 75° C., preferably from 30° to 50° C. The amount of acid should be from about 0.01 mole to 1 mole per mole of product IV. Excess molar amounts may be used. When only very small amounts (0.01 to 0.15 mole) is used the free amine product, serinol is formed while when large amounts of acid is used the amine salt is the resultant product. Serinol is recovered from the solution as the solid salt if one mole of acid is used. It is readily separated by filtration, by evaporation of the liquid solvent, or other conventional means. If only a catalytic amount of acid is used, the serinol formed can be removed by distillation.

The subject process provides a new route for the production of serinol using readily available and easily attainable reactants. The process requires conventional handling conditions which do not present any problems which may result in catastrophic results, such as encountered by the present commercial mode of forming serinol.

The present process provides a means of converting 5-nitro-1,3-dioxane derivative's into serinol by catalytic hydrogenation under certain conditions which retain the dioxane ring while reducing the nitro group and then hydrolyzing the resultant amino derivative. Further, the present invention provides a process for synthesizing serinol starting with nitromethane and without encountering the hazardous material, sodium bis(-hydroxymethyl)nitromethane, of the present commercial process.

The following examples are given for illustrative purposes only and are not meant to be a limitation on the invention as defined by the claims appended hereto. All parts and percentages are by weight unless otherwise indicated.

EXAMPLE 1

A 100 ml round bottom flask equipped with a stir bar and reflux condenser topped with a nitrogen inlet was charged with 15.1 g (0.1 mol) of tris(hydroxymethyl)nitromethane and 22 ml (0.3 mol) of acetone. The mixture was heated until all the tris(hydroxymethyl)nitromethane had dissolved and then was cooled to 15°-20° C. The trimethylol compound crystallized in fine needles. Boron trifluorideetherate (13 ml, 0.1 mol) was added with stirring. The temperature rose to 55° C. and crystals of product began to separate. After five minutes, the mixture was poured into a stirred mixture of 110 ml of saturated sodium bicarbonate solution and excess ice. After stirring for 15 minutes, the product, 2,2-dimethyl-5-hydroxymethyl-5-nitro-1,3-dioxane was collected by filtration, washed with cold water and dried in vacuo. The yield was determined to be 88%.

EXAMPLE 2

To a 100 ml round bottom flask equipped with a stir bar, soxhlet extractor and reflux condenser topped with a nitrogen inlet was added 2 g (0.013 mol) tris(hydroxymethyl)nitromethare, 1.42 g (0.014 mol) cyclohexanone, 0.2 g p-toluenesulfonic acid and 60 ml acetonitrile. The soxhlet thimble was filled with 3A molecular sieves. The reaction mixture was then refluxed for 24 hours with the sieves being changed at 6 hours. After cooling to room temperature, all volatiles were removed in vacuo. The solid remaining was then dissolved in 30 ml $CH_2Cl_2$ and dried over $MgSO_4$. After one hour, the $MgSO_4$ was filtered off and the $CH_2Cl_{12}$ removed to give 2,2-pentamethylene-5-hydroxymethyl-5-nitro-1,2-dioxane in 73% yield.

EXAMPLE 3

Into a 250 ml round bottom flask equipped with a stir bar, thermometer and reflux condenser topped with a nitrogen inlet was added 5.73 (0.03) mole) of 2,2-dimethyl-5-hydroxymethyl-5-nitro-1,3-dioxane and 70 ml 10% sodium hydroxide which was heated to 60° C. for one hour. The solution was cooled to 5° C. and at this temperature acidified to pH 5 with concentrated acetic acid. The precipitated solid was filtered off and dried to give 5.2 g (92%) of 2,2-dimethyl-5-nitro-1,3-dioxane m.p. 60°-61° C. $^1$H NMR in $CD_3OD$ also confirmed the structure.

EXAMPLE 4

The reaction was run as described in Example 3 except that 2,2-pentamethylene-5-hydroxymethyl-5-nitro-1,3-dioxane was used instead of 2,2-dimethyl-5-hydroxymethyl-5-nitro-1,3-dioxane. The yield of product 2,2-pentamethylene-5-nitro-1,3-dioxane was 81%.

EXAMPLE 5

To a 125 cc high pressure reactor was added 0.5 g (0.003 mol) 2,2-dimethyl-5-nitro-1,3-dioxane, 250 mg RaNi and 20 ml ethanol. The reactor was then pressurized with 100 psi hydrogen and heated to 80° C. for 12 hrs. After cooling to room temperature the volatiles were removed in vacuo. The oily residue remaining (0.41 g, 89% yield) was shown to be 2,2-dimethyl-5-amino-1,3-dioxane by $^1$H NMR.

EXAMPLE 6

The reaction was run as described in Example 5 except that 2,2-pentamethylene-5-nitro-1,3-dioxane was used instead of 2,2-dimethyl-5-nitro-1,2-dioxane. The yield of product was 76%.

EXAMPLE 7

To a 50 ml round bottom flask equipped with a stir bar and reflux condenser topped with a nitrogen inlet was added 0.5 g (0.004 mol) 2,2-dimethyl-5-amino-1,3-dioxane, 10 ml methanol and 0.3ml concentrated HCl. The reaction was heated to 35°-40° C. for 1 hour. After cooling to room temperature, the volatiles were removed to give the hydrochloride salt of Serinol in 92% yield.

EXAMPLE 8

220 mg 5% Pd/C was added to a solution of 500 mg 2,2-dimethyl-5-nitro-1,3-dioxane (3.1 mmoles) in 30 ml methanol. Ammonium formate (985 mg, 15.6 mmoles) was then added, and the mixture was refluxed for three hours. The reaction solution was then filtered, and the filtrate concentrated in vacuo to yield 286 mg 2,2-dimethyl-5-amino-1,3-dioxane (70% yield).

EXAMPLE 9

Following the procedure 2(A) described in this application, to a 100 ml round bottom flask equipped with a stir bar and reflux condenser topped with a nitrogen inlet was added 5 g (0.03 mol) tris(hydroxymethyl)nitromethane, 2.86 g (0.04 mol) ethylvinyl ether, 50 ml acetonitrile and 5 drops concentrated HCl. The reaction was heated to 35°-40° C. for 4 hours. After cooling to room temperature the volatiles were removed to give the product, 2-methyl-5-hydroxymethyl-5-nitro-1,3-dioxane, in 86% yield. $^1$H NMR in $CD_3OD$ confirmed the structure.

EXAMPLE 10

Following the procedure 2(B) described in this application; to a 25 ml round bottom flask equipped with a stir bar was added 1 g (0.007 mol) tris(hydroxymethyl) nitormethane, 8 ml (0.07 mol) 2,2-diemthoxypropane and 2 drops concentrated hydrochloric acid. The reaction was heated to 45°-50° C. for 30 minutes. After cooling to room temperature the volatiles were removed in vacuo to give a white solid 2,2-dimethyl-5-hydroxy methyl-5-nitro-1,3-dioxane in 93% yield.

EXAMPLE 11

The reaction was run as described in Example 5; except that water was used as the solvent instead of ethanol. The yield of product 2,2-dimethyl-5-amino-1,3-dioxane was 89%.

EXAMPLE 12

To a 250 ml round bottom flask equipped with a stir bar was added 5 g (0.03 mol) tris(hydroxymethyl) nitromethane, 3.75 g (0.36 mol) 2,2-dimethoxypropane, 100 ml acetonitrile and 6 drops concentrated hydrochloric acid. The reaction was heated to 80° C. for 18 hours. After cooling to room temperature tte volatiles were removed in vacuo to give a white solid 2,2-dimethyl-5-hydroxy methyl-5-nitro-1,3-dioxane in 82% yield.

This example is an alternate procedure to that used in Example 10 (which was run neat). This procedure used a solvent and required longer reaction time and higher temperatures.

We claim:

1. A process of forming 2-amino-1,3-propanediol which comprises
   (a) reacting nitromethane with formaldehyde in a molar ratio of at least 3 moles of formaldehyde for each mole of nitromethane, said reaction conducted in the presence of a base to form tris(hydroxymethyl)-nitromethane(I);
   (b) reacting (I) with a ketone of the formula

in the presence of an acid and under conditions to remove water by-product formed to produce a 5-nitro-5-hydroxymethyl-1,3-dioxane compound (II) of the formula

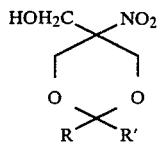

wherein each R and R' are independently from alkyl, cycloalkyl or aryl groups or R and R' together represent an alkylene group;
   (c) reacting (II) with an alkali metal hydroxide at elevated temperature and neutralizing said alkali metal with an organic acid at a temperature of less than about 20° C. to produce 5-nitro-1,3-dioxane derivative (III) of the corresponding (II) reactant;
   (d) reacting (III) under reducing conditions to produce the 5-amino-1,3-dioxane derivative (IV) of the corresponding (III) reactant; and
   (e) hydrolyzing (IV) by contacting a solution of (IV) with an acid to produce 2-amino-1,3-propanediol.

2. A processing of forming 2-amino-1,3-propanediol which comprises
   (a) reacting nitromethane with formaldehyde in a molar ratio of at least 3 moles of formaldehyde for each mole of nitromethane, said reaction conducted in the presence of a base to form tris(hydroxymethyl) nitromethane(I);
   (b) reacting (I), in the presence of a strong acid, with an ether compound selected from (a) a vinyl alkyl ether of the formula CH$_2$=CHOR or (b) a gem diether of the formula

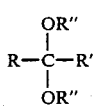

to produce a 5-nitro-5-hydroxymethyl-1,3-dioxane of the formula:

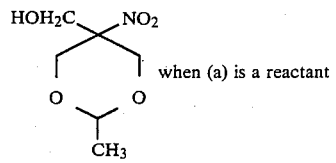

when (a) is a reactant or

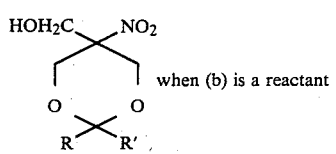

when (b) is a reactant wherein each R and R' are independently selected from alkyl, cycloalkyl or aryl groups or R and R' together represent an alkylene group and R" is selected from alkyl;
   (c) reacting (II) with an alkali metal hydroxide at elevated temperatures and neutralizing said alkali metal with an organic acid at a temperature of less than about 20° C. to produce 5-nittro-1,3-dioxane derivative (III) of the corresponding (II) reactant;
   (d) reacting (III) under reducing conditions to produce the 5-amino-1,3-dioxane derivative (IV) of the corresponding (III) reactant; and
   (e) hydrolyzing (IV) by contacting a solution of (IV) with an acid to produce 2-amino-1,3-propanediol.

3. The process of claim 1 wherein the ketone is selected from a low boiling ketone and a dessicant is present to remove water or the ketone is selected from a high boiling ketone and water is removed by distillation.

4. The process of claim 2 wherein the ether is selected from ethyl vinyl ether, 2,2-dimethoxypropane, 2,2-diethoxypropane, 3,3-dimethoxypentane and 3,3-diethoxypentane.

5. The process of claim 3 or 4 wherein in (d) the reducing conditions comprise contacting (III) with hydrogen and a catalyst selected from Raney nickel, supported rhodium, supported palladium or supported platinum at a temperature of from about 30° C. to about 100° C. and under a hydrogen pressure of from about 25 psi to about 100 psi; and in (e) hydrolyzing comprises contacting a solution of (IV) with an acid selected from mineral acids or strong organic acids.

6. The process of claim 5 wherein in (d) the catalyst is Raney nickel.

7. The process of claim 5 wherein in (d) the catalyst is selected from rhodium, palladium or platinum on a carbon support.

8. The process of claim 3 or 4 wherein in (d) the reducing conditions comprise contacting said 5-nitro-1,3-dioxane derivative (IV) with ammonium formate in the presence of a supported palladium catalyst.

9. The process of claim 5 wherein in (d) the 5-nitro-1,3-dioxane derivative (IV) and the catalyst are contacted by slurrying the catalyst in a solution of dioxane compound.

10. The process of claim 5 wherein in (d) the 5-nitro-1,3-dioxane derivative (IV) and the catalyst are contacted by passing a solution of (IV) through a packing which contains said catalyst.

* * * * *